United States Patent
Stanslaski et al.

(10) Patent No.: US 11,103,172 B2
(45) Date of Patent: Aug. 31, 2021

(54) DEVICES AND METHODS FOR SENSING PHYSIOLOGICAL SIGNALS DURING STIMULATION THERAPY

(71) Applicant: Medtronic, Inc., Minneapolis, MN (US)

(72) Inventors: Scott R. Stanslaski, Shoreview, MN (US); Peng Cong, Plymouth, MN (US); Wesley A. Santa, Andover, MN (US); Timothy J. Denison, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1565 days.

(21) Appl. No.: 14/064,801

(22) Filed: Oct. 28, 2013

(65) Prior Publication Data

US 2015/0119751 A1    Apr. 30, 2015

(51) Int. Cl.
*A61B 5/04* (2006.01)
*A61N 1/36* (2006.01)
(Continued)

(52) U.S. Cl.
CPC .............. *A61B 5/24* (2021.01); *A61N 1/3605* (2013.01); *A61B 5/40* (2013.01); *A61B 5/7217* (2013.01);
(Continued)

(58) Field of Classification Search
CPC .... A61N 1/3605; A61N 1/36; A61N 1/36125; A61B 5/04001; A61B 5/4836; A61B 5/7225; A61B 5/40; A61B 5/7217
See application file for complete search history.

(56) References Cited

U.S. PATENT DOCUMENTS

| 4,151,513 A | 4/1979 | Menken et al. |
| 4,722,343 A | 2/1988 | Lombardi |

(Continued)

FOREIGN PATENT DOCUMENTS

EP    1384434    1/2004

OTHER PUBLICATIONS

PCT/US2014/055553 Invitation to Pay Fees and Communication Relating to the Results of a Partial International Search Report, Nov. 27, 2014.
(Continued)

*Primary Examiner* — Rene T Towa
(74) *Attorney, Agent, or Firm* — Withers & Keys, LLC (57) ABSTRACT

Devices and methods provide for the sensing of physiological signals during stimulation therapy by preventing stimulation waveform artifacts from being passed through to the amplification of the sensed physiological signal. Thus, the amplifiers are not adversely affected by the stimulation waveform and can provide for successful sensing of physiological signals between stimulation waveform pulses. A blanking switch may be used to blank the stimulation waveform artifacts where the blanking switch is operated in a manner synchronized with the stimulation waveform so that conduction in the sensing path is blocked during the stimulation pulse as well as during other troublesome artifacts such as a peak of a recharge pulse. A limiter may be used to limit the amplitude of the sensed signal, and hence the stimulation artifacts, that are passed to the amplifier without any synchronization of the limiter to the stimulation waveform.

12 Claims, 12 Drawing Sheets

(51) Int. Cl.
*A61B 5/24* (2021.01)
*A61B 5/00* (2006.01)

(52) U.S. Cl.
CPC ......... *A61B 5/7225* (2013.01); *A61N 1/36125* (2013.01)

(56) References Cited

U.S. PATENT DOCUMENTS

| | | | |
|---|---|---|---|
| 5,172,690 | A | 12/1992 | Nappholz et al. |
| 5,843,136 | A * | 12/1998 | Zhu ................ A61N 1/3712 607/13 |
| 6,044,296 | A * | 3/2000 | Zhu ................ A61N 1/3712 607/13 |
| 6,058,327 | A * | 5/2000 | Borgerding ........ A61N 1/36507 607/9 |
| 6,169,921 | B1 * | 1/2001 | KenKnight ........ A61N 1/3712 607/28 |
| 6,324,425 | B1 * | 11/2001 | Blow ................ A61N 1/3627 607/13 |
| 6,473,649 | B1 | 10/2002 | Gryzwa |
| 6,615,089 | B1 * | 9/2003 | Russie ............ A61N 1/368 607/28 |
| 7,024,241 | B1 * | 4/2006 | Bornzin ............ A61N 1/362 607/9 |
| 8,249,708 | B2 | 8/2012 | Krause et al. |
| 8,295,934 | B2 | 10/2012 | Leyde |
| 8,335,664 | B2 | 12/2012 | Eberle |
| 2002/0049476 | A1 * | 4/2002 | Bardy ................ A61N 1/362 607/5 |
| 2006/0136003 | A1 * | 6/2006 | Hudson ............ A61N 1/368 607/28 |
| 2006/0287609 | A1 | 12/2006 | Litvak et al. |
| 2007/0178579 | A1 | 8/2007 | Ross |
| 2007/0198066 | A1 | 8/2007 | Greenberg et al. |
| 2008/0064934 | A1 | 3/2008 | Frei et al. |
| 2008/0269836 | A1 | 10/2008 | Foffani |
| 2010/0069996 | A1 | 3/2010 | Strahl |
| 2010/0222844 | A1 | 9/2010 | Troosters et al. |
| 2010/0324618 | A1 * | 12/2010 | Wanasek ............ A61N 1/3625 607/9 |
| 2012/0283795 | A1 * | 11/2012 | Stancer ............ A61N 1/3688 607/11 |
| 2013/0138170 | A1 | 5/2013 | Ternes et al. |

OTHER PUBLICATIONS

Merletti, Roberto, Ph.D. and Marco Knaflitz, Ph.D., "Electrically Evoked Myoelectric Signals", Critical Reviews in Biomedical Engineering, 19(4):293-340 (1992).
PCT/US2014/055553 International Search Report and Written Opinion, dated Mar. 4, 2015.
EP 14 777980.5—EP Communication—Examining Division dated Nov. 4, 2019.
EP 14 777980.5—EP Communication—Annex Examining Division dated Nov. 4, 2019.
EP 14 777980.5—EP Communication—Decision to Grant, dated Feb. 11, 2021.

* cited by examiner

FIG. 9

DEVICES AND METHODS FOR SENSING PHYSIOLOGICAL SIGNALS DURING STIMULATION THERAPY

TECHNICAL FIELD

Embodiments provide devices and methods for sensing physiological signals. More particularly, embodiments provide devices and methods for sensing physiological signals while stimulation therapy is being conducted in proximity to the location where the physiological signals are being sensed.

BACKGROUND

Electrical stimulation therapy may be used for various forms of treatment. For example, stimulation therapy may be provided to address neurological issues such as chronic pain, tremors, and the like. In such an example, an implantable stimulation device is typically located in one location of convenience and is connected to electrical leads that are routed to a stimulation site such as within the brain, within the spinal column, within the pelvic region, or elsewhere. The electrical leads include electrodes that interface with the tissue at the stimulation site to deliver the stimulation signals from the stimulation device.

It may be useful to also sense physiological signals nearby the stimulation site. Such signals may be useful to tailor the stimulation therapy to the particular condition being treated and/or to better understand the response of the tissue nearby the stimulation site to the stimulation signals. Sensing physiological signals may be especially useful where the stimulation therapy may be at least partially controlled based on the physiological signals.

Sensing physiological signals in proximity to the stimulation site while the stimulation signals are being applied is problematic. The sensing electrodes receive the physiological signals with amplitudes in the microvolt range while also receiving the stimulation signals that have amplitudes reaching tens of volts. Thus, the physiological signal is too small relative to the stimulation signal to be detected. Additionally, the relatively large amplitudes of the stimulation pulse and recharge pulse of the stimulation signal can produce lingering voltages within the sensing circuits that overly saturate the sensing circuits and cause the physiological signals to be obscured even during periods when the stimulation pulse and the recharge pulse are not present.

This is particularly troubling for neurological stimulation systems. In neurological stimulation, the recharge phase occupies the majority of the time between stimulation pulses. For instance, a neurological stimulation signal may have a period of 7 milliseconds while the recharge phase occupies 5 of the 7 milliseconds milliseconds. Thus, it is not feasible to simply blank out the sensing of the stimulation pulse and the recharge phase because there is an inadequate amount of time remaining within the period to sense the physiological signal.

SUMMARY

Embodiments address issues such as these and others by providing devices and methods that prevent the voltages of the stimulation signal from affecting the sensing circuits even for neurological systems. Some embodiments provide blanking of the sensed physiological signal during the high amplitude portions of the stimulation signal while allowing physiological sensing to proceed during the lower amplitude portions. Some embodiments provide for amplitude limiting of the sensed physiological signal.

Embodiments provide a method of sensing physiological signals while stimulation therapy is being provided. The method involves, while a stimulation signal having a stimulation phase and a recharge phase is being output from a first electrode at a stimulation site, sensing a physiological signal at a second electrode in proximity to the stimulation site to produce a sensed signal. The method further involves, during the stimulation phase of the stimulation signal, blanking the sensed signal.

Embodiments provide a device for sensing a physiological signal while stimulation therapy is being provided. The device includes a sensing electrode, a blanking switch, and an electrically conductive pathway connected between the sensing electrode and a blanking switch. The device further includes a sensing amplifier and a filter between the blanking switch and the sensing amplifier. The device also includes a controller that maintains the blanking switch in a non-conducting state during a stimulation phase of a stimulation signal and may include at least a portion of the recharge phase of the stimulation signal.

Embodiments provide a method of sensing physiological signals while providing stimulation therapy. The method involves, while a stimulation signal having a stimulation phase and a recharge phase is being output from a first electrode at a stimulation site, sensing a physiological signal at a second electrode in proximity to the stimulation site. The method further involves, while sensing the physiological signal, limiting an amplitude of the sensed signal. Limiting the amplitude of the sensed signal may comprise including a voltage limiter between the second electrode and a filter. The filter may comprise a low pass filter and a high pass filter. Limiting the amplitude of the sensed signal may also comprise setting a threshold amplitude.

Embodiments provide a device for sensing a physiological signal while stimulation therapy is being provided. The device includes a sensing electrode, a signal limiter, and an electrically conductive pathway connected between the sensing electrode and the signal limiter. The device also includes a sensing amplifier electrically coupled to the signal limiter. The device may further comprise a controller that sets an amplitude threshold of the signal limiter. The device may also further comprise a low pass filter and a high pass filter located electrically between the signal limiter and the voltage amplifier.

DETAILED DESCRIPTION

Embodiments provide medical devices and related methods that minimize the effects of stimulation signal artifacts on a sensed signal. Some embodiments blank the sensed signal during the peaks of the stimulation signal, such as the entire stimulation pulse and the peak of the recharge pulse, in order to remove the artifacts. Some embodiments limit that amplitude of the sensed signal in order to remove the peaks of the stimulation signal from the sensed signal.

Figure 1:
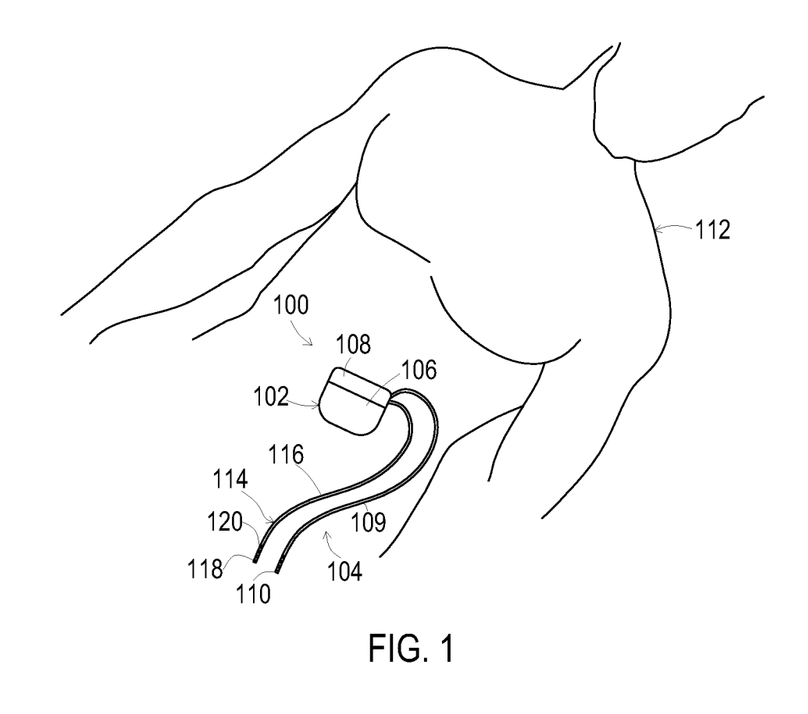
FIG. 1 shows a patient having an example of an implantable medical system for sensing physiological signals concurrently with providing stimulation signals according to various embodiments.

FIG. 1 shows an example of an operating environment for the various embodiments. An implantable medical system 100 is implanted within a body of a patient 112. The implantable medical system 100 includes a stimulation and sensing device 102 coupled to a stimulation lead 104. The stimulation and sensing device 102 includes a conductive outer casing 106 as well as a header 108 that includes a bore where a proximal end of the stimulation lead 104 is positioned. The stimulation lead 104 includes a lead body 109 and one or more electrodes 110 on a distal end of the lead body 109 which is positioned at a stimulation site within the body of the patient 112. The stimulation device 102 produces stimulation signals that are delivered through conductors of the stimulation lead 104 to the electrodes 110 where those stimulation signals enter the tissue of the patient 112.

In this example, the header 108 also includes a bore where a proximal end of a sensing lead 114 is positioned. The sensing lead 114 includes a lead body 116 and one or more electrodes 118, 120 that are positioned in proximity to the stimulation site within the body of the patient 112 so as to be able to capture physiological signals emanating from the stimulation site. The stimulation and sensing device 102 senses the physiological signals, and the sensing function either blanks or limits the stimulation signal that is captured during periods of stimulation as discussed in more detail below.

The foregoing example provides stimulation lead 104 dedicated to providing the stimulation signal and sensing lead 114 dedicated to sensing the physiological signal. In still another example, the same one or more leads may be used to provide both the stimulation and sensing function. For instance, one or more electrodes of a single lead may be used to deliver stimulation signals to the tissue of patient 112 and one or more different electrodes of that same lead may be used to sense physiological signals emanating from the stimulation site. Alternatively, multiple electrodes residing on multiple leads may be used to deliver the stimulation signals while one or more electrodes provided by one or both of the multiple leads may be used to sense the physiological signals. In such cases, the lead is electrically connected to both the stimulation engine and the sensing circuit, this option being shown as dashed lines in FIG. 2 discussed below.

While the examples discussed herein include both the sensing and stimulation functions within one device 102, it will be appreciated that a separate device could instead be used for sensing such that there is a first device for stimulation and a second device for sensing. In that case, the lead 114 is connected to the separate device which then performs the sensing function including the various aspects discussed below including blanking or limiting the stimulation signal being provided from the electrodes 110. The separate device may use a stimulation signal blanking function if that separate device is synchronized to the operation of the stimulation device. If the separate device utilizes a stimulation signal limiting function, then no synchronization is necessary to the stimulation device.

The one or more leads used for providing the stimulation signals and for sensing the physiological signals may be of various types. In one example, a lead having a simple electrode array geometry may be used for stimulation and/or for sensing. An example of a simple electrode array geometry may include one or more ring electrodes distributed at different axial positions along the length of a lead. Another example of a simple electrode array geometry is a planar array of electrodes on a paddle lead.

In another embodiment, one or more leads used for providing the stimulation signal and for sensing the physiological signals may have a complex electrode array geometry. A complex electrode array geometry generally refers to an arrangement of stimulation electrodes at multiple non-planar or non-coaxial positions, in contrast to simple electrode array geometries in which the electrodes share a common plane or a common axis. An example of a complex electrode array geometry, in accordance with this disclosure, is an array of electrodes positioned at different axial positions along the length of a lead, as well as at different angular positions about the periphery, e.g., circumference, of the lead. In some embodiments, the electrodes in the complex array geometry may appear similar to non-contiguous, arc-like segments of a conventional ring electrode. A lead with a complex electrode array geometry may include multiple "rings" of such electrode segments. Each ring is disposed at a different axial position. Each electrode segment within a given ring is disposed at a different angular position. The lead may be cylindrical or have a circular cross-section of varying diameter. Such a lead may be referred to as a "segmented" lead.

Another example of a complex electrode array geometry is an array of electrodes positioned on multiple planes or faces of a lead. As an illustration, arrays of electrodes may be positioned on opposite planes of a paddle lead or multiple faces of a lead having a polygonal cross-section. Examples of complex array geometries are shown and described in U.S. Pat. No. 7,822,483 entitled "Electrical and Activation Field Models for Configuring Stimulation Therapy" which is assigned to the assignee of the present application and which is incorporated herein by reference. Other types of sensing and/or stimulation electrodes may be used according to the current disclosure, including conformable electrodes, cuff electrodes, segmented electrodes, or any other type of electrodes capable of forming unipolar, bipolar or multi-polar electrode configurations.

The stimulation signals may be delivered using various electrode arrangements such as unipolar arrangements, bipolar arrangements or multipolar arrangements. A unipolar stimulation arrangement generally refers to the use of an anode on the conductive outer casing 106 that sources current and one or more cathodes on one or more leads (e.g., 104, 114) that sink current. A bipolar stimulation arrangement generally refers to the use of an anode on a lead (e.g., lead 104) that sources current and a cathode on the same lead and/or another lead that sinks current. A multipolar stimulation arrangement generally refers to the use of more than one anode on a lead (e.g., lead 104) that each source current and one or more cathodes on the same lead or another lead that sink current, or the use of one anode on a lead that sources current and multiple cathodes on the same lead or another lead that sink current.

A hybrid stimulation arrangement that combines both unipolar and bipolar electrode relationships may be referred to as an omnipolar arrangement. In an omnipolar arrangement, an anode on the housing may be used to deliver stimulation pulses substantially simultaneously with at least one anode on a lead and at least one cathode on a lead. In this case, for an omnipolar arrangement, at least one anode on a lead and at least one anode on the housing can be used simultaneously in combination with at least one cathode on a lead. In other omnipolar arrangements, a cathode on the housing may be used to deliver stimulation pulses substantially simultaneously with at least one cathode on a lead and at least one anode on a lead. In this alternative case, for an omnipolar arrangement, at least one cathode on a lead and at least one cathode on the housing can be used simultaneously in combination with at least one anode on a lead. Any of the above electrode arrangements, or other electrode arrangements, may be used to deliver electrical stimulation in accordance with techniques described in this disclosure.

Figure 2:
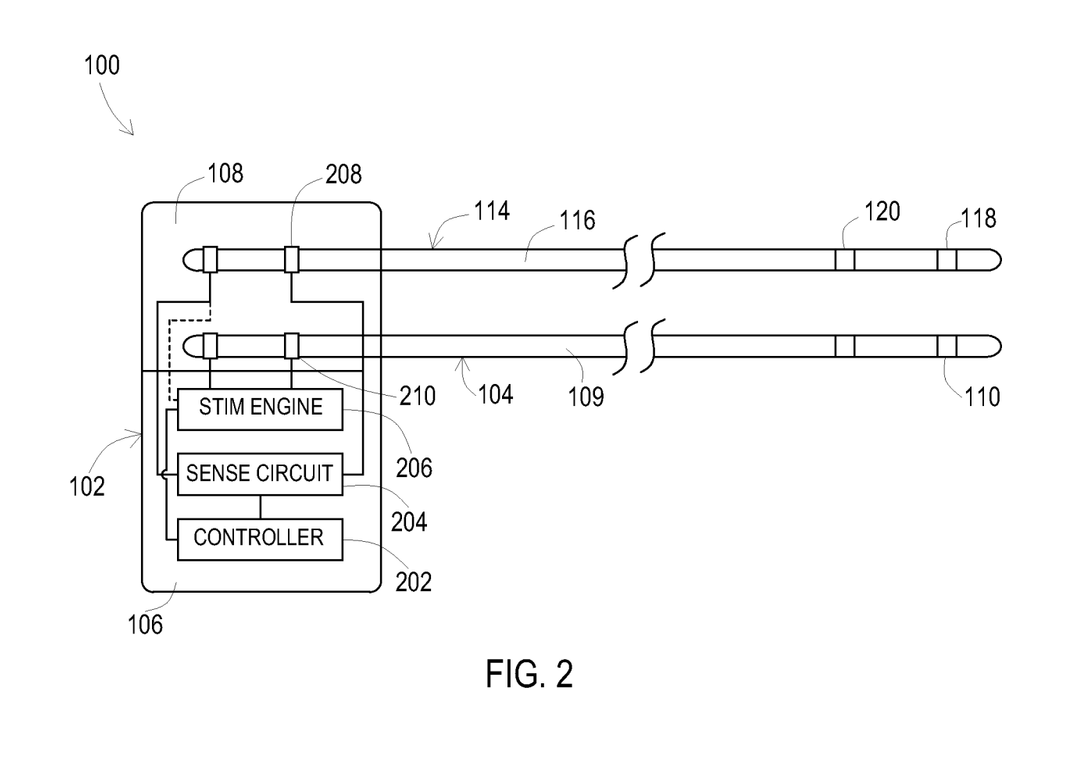
FIG. 2 shows an implantable medical system including a medical device attached to a stimulation lead and a sensing lead or to a sensing and stimulation lead.

FIG. 2 shows the implantable medical system 100 in more detail. Here, the stimulation device 102 includes a stimulation engine 206, a sensing circuit 204, and a controller 202. A conventional stimulation engine 206 produces the stimulation pulses and recharge pulses applied to the stimulation pathway via electrical connections 210 to the stimulation lead 104 within the header block 108. The sensing circuit 204 captures the physiological signals via connections 208 to the sensing lead 114 within the header block 108. In an embodiment where the sensing and stimulation function are provided by one or more of the same leads, both the stimulation engine 206 and sense circuit 204 may be coupled to the same one or more leads, as appropriate. Such an option is illustrated for the lead 114 of FIG. 2 with a dashed line indicating the optional electrical connection of the stimulation engine 206 being electrically connected to the lead 114 where one of the electrodes 118 or 120 is being used for stimulation while the other electrode is being used for sensing.

The sensing circuit 204 captures the physiological signals in proximity to the stimulation site by either blanking the stimulation signal or by limiting the amplitude of the sensed stimulation signal. In either case, the stimulation signal does not negatively impact the sensing circuit 204 such that the sensing circuit 204 can capture accurate physiological data during the time between the stimulation pulses.

In this example, the controller 202 orchestrates the operation of the sensing circuit 204 and the stimulation engine 206. The controller 202 activates and deactivates various phases of operation of the stimulation that occur during stimulation therapy. The phases may include a stimulation output phase where the stimulation pulse is delivered, and a recharge phase that clears voltage on coupling capacitors in the stimulation path within the stimulation engine 206. Likewise, the controller 202 activates blanking switches of the sensing circuit 204 to blank the stimulation signal and at least a portion of a passive recharge signal such as the peak of the passive recharge signal when a passive recharge signal is used as discussed below in relation to FIG. 5A. For an active recharge signal, some or all or none of the passive recharge signal may be blanked, depending upon the type of active recharge signal as discussed below in relation to FIGS. 5B and 5C. Alternatively, the controller 202 controls the threshold being applied by signal limiters of the sensing circuit 204 to limit the signal amplitude, such as the voltage, of the stimulation signal and recharge signal being captured.

The controller 202 may be of various forms. For instance, the controller 202 may comprise a general purpose programmable processor that implements programming instructions to bring about the operation of the stimulation engine 206 and the sensing circuit 204. As other examples, the controller 202 may comprise a dedicated purpose processor and/or hardwired digital logic.

Figure 3:
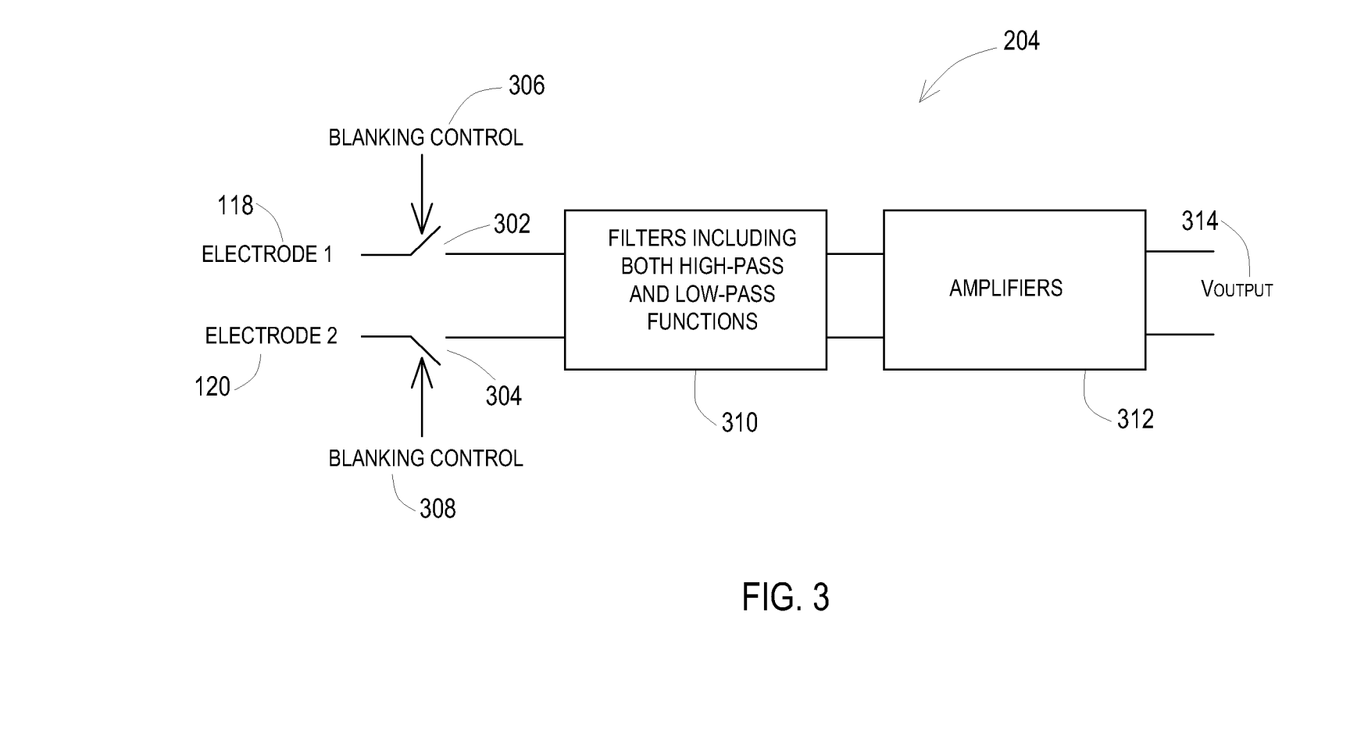
FIG. 3 shows an example of sensing circuitry of a medical device that blanks the sensed signal during the peaks of the stimulation signal.

FIG. 3 shows an example of the sensing circuit 204 that blanks the stimulation signal and the peak of the recharge signal. Each sensing electrode 118, 120 is electrically coupled to a blanking switch 302, 304 that is controlled by the controller 202. The blanking switches may be implemented in silicon such as individual transistors or in more complex arrangements as discussed below. The controller 202 provides a blanking control signal 306, 308 that causes the switches to either conduct signals or stop conducting the signals from the electrodes 118, 120. The switches 302, 304 conduct from a time after the peak of the recharge phase to a time before the beginning of the next stimulation phase and stop conducting at least during the stimulation phase and the peak of the following recharge phase in order to blank the stimulation artifacts from the sensed signal.

The blanking switches 302, 304 are each followed in the respective signal path by filters 310 that include both high pass and low pass filters that remove extraneous frequencies from the sensed signal. Examples of the filters 310 are discussed below in relation to FIGS. 4A and 4B. The filtered signals are provided as input to conventional amplifiers 312 that scale the amplitude as desired to produce the sensed signal output 314. The filters 310 include a high pass filter to decouple from DC which can occur during the blanking period. The filters 310 include a low pass filter to avoid waveform spread and to avoid a rectification effect from high frequency interferences.

Figure 4A:
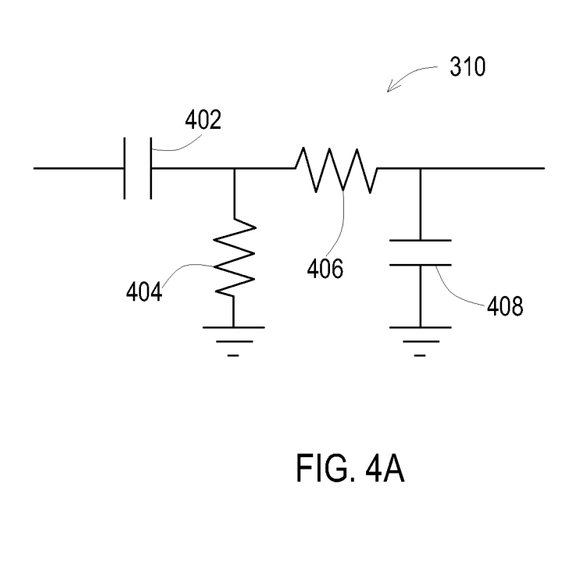
FIGS. 4A and 4B show examples of filters that may be used in the sensing circuitry of FIG. 3.
Figure 4B:
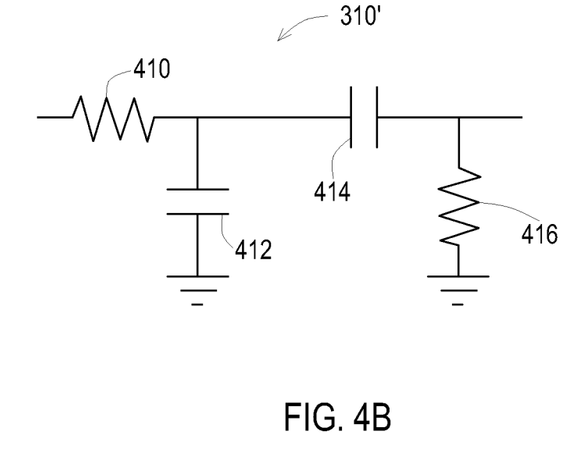

In one example, the filter 310 of a given sensing signal path utilizes a high pass filter immediately following the blanking switch 302 or 304 followed by a low pass filter as shown in FIG. 4A. A series capacitor 402 and parallel-to-ground resistor 404 form the high pass filter which immediately follows the blanking switch 302 or 304 while the series resistor 406 and parallel-to-ground capacitor 408 form the low pass filter which is followed by the amplifier 312. As shown in FIG. 4B, the order may be reversed in an alternative filter 310' where the low pass filter formed by the series resistor 410 and parallel-to-ground capacitor 412 immediately follow the blanking switch 302 or 304. The high pass filter formed by the series capacitor 414 and parallel-to-ground resistor 416 is then followed by the amplifier 312. In relation to these filters 310, a resistor may also be placed before the blanking switches 302, 304 for added safety.

Figure 5A:
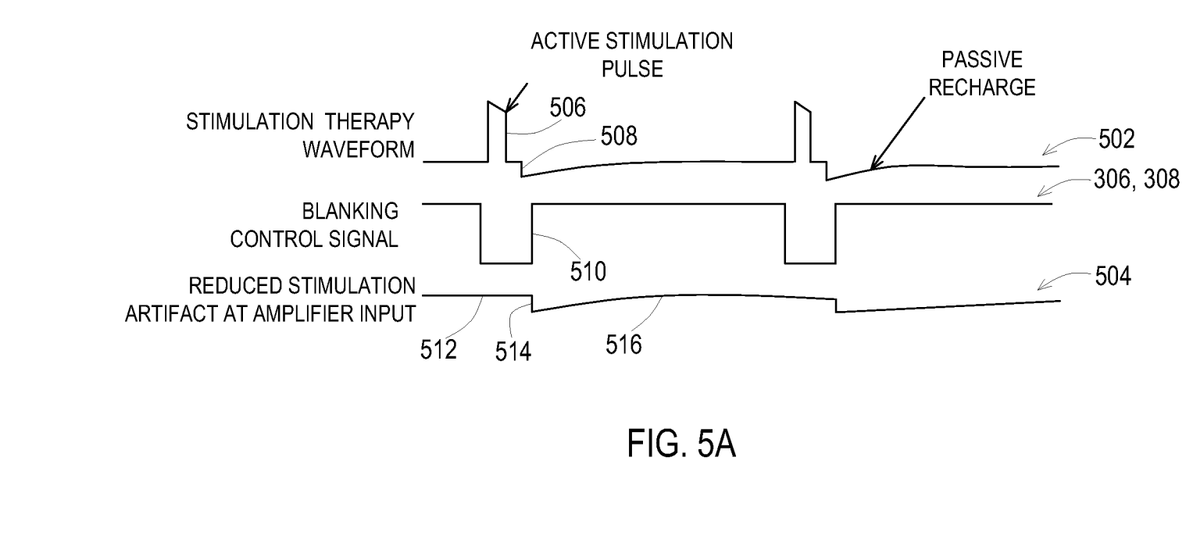
FIG. 5A shows a first example of the stimulation waveform, blanking signal, and the resulting artifact on the sensed signal.

FIG. 5A shows a set of signals and their related timing including the stimulation therapy waveform 502, the blanking control signal 306, 308, and the signal 504 that is provided to the amplifiers 312. As can be seen, the stimulation therapy waveform 502 includes a stimulation pulse 506 followed by a passive recharge pulse 508 of opposite polarity with a lower amplitude and longer settling time. The recharge pulse could instead be active and in that case could more closely match the amplitude and settling time of the stimulation pulse, which is discussed in a separate example below in FIG. 5B.

The blanking control signal 306, 308 is held at an amplitude that biases the blanking control switches to the conducting state to allow current flow. However, the blanking control signal 306, 308 includes an inverted pulse 510 that unbiases the blanking control switches from the conducting state to the non-conducting state to prohibit current flow. The blanking control signal 306, 308 is synchronized in time to the stimulation waveform 502 such that the blanking control signal inverted pulse 510 begins just before the stimulation pulse 506 and terminates just after stimulation pulse or after the peak of the recharge pulse 508. The blanking control signal inverted pulse 510 thereby causes current flow to be blocked during the entire stimulation pulse 506 and/or during the peak of the recharge pulse 508 to produce the signal 504 once filtered. The signal 504 eliminates the artifacts from the stimulation pulse 506 as indicated by the region 512. Region 514 includes the smaller artifact 514 from the tail of the recharge pulse 508 which is not large enough to saturate the filters 310 and amplifiers 312. Therefore, the sensed physiological signals are present and recorded in the region 516 upon the recharge pulse 508 having adequately settled soon after the peak.

Figure 5B:
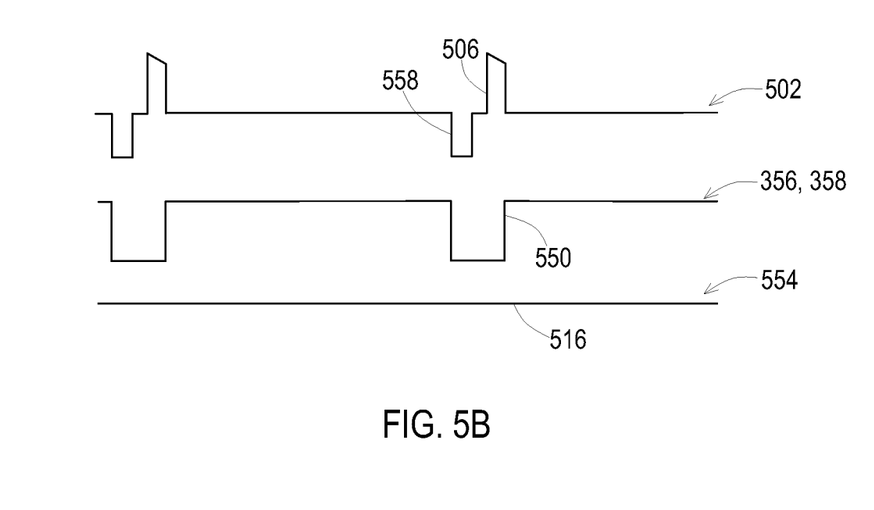
FIG. 5B shows a second example of the stimulation waveform, blanking signal, and the resulting artifact on the sensed signal.

FIG. 5B shows a set of signals and their related timing including the stimulation therapy waveform 502, the blanking control signal 356, 358, and the signal 554 that is provided to the amplifiers 312. As can be seen, the stimulation therapy waveform 502 includes a stimulation pulse 506 followed by an active recharge pulse 558 of opposite polarity with a lower amplitude and longer duration. By using active recharge, the recharge pulse 558 may be provided with a steady amplitude rather than decaying like the passive recharge pulse. The active recharge pulse may also have a larger amplitude than the peak of the passive recharge pulse. In either case, active recharge provides the option to shorten the duration of the active recharge pulse relative to the passive recharge pulse if desired and also allows the start and stop time of the recharge pulse to be chosen as desired. In this example, it has been chosen to start the active recharge pulse 558 well after the end of the stimulation pulse 506 so that sensing may occur very shortly after the end of the stimulation pulse 506 which allows for sensing of evoked compound potential (EVCP) or other stimulation induced biological signals of interest, e.g. Electromyography (EMG).

The blanking control signal 356, 358 is held at an amplitude that biases the blanking control switches to the conducting state to allow current flow. However, the blanking control signal 356, 358 includes an inverted pulse 550 that unbiases the blanking control switches from the conducting state to the non-conducting state to prohibit current flow. The blanking control signal 356, 358 is synchronized in time to the stimulation waveform 502 such that the blanking control signal inverted pulse 550 begins just before the active recharge pulse 558, which is well after the EVCP or other signal of interest. Alternatively, the inverted pulse 550 could occur sometime after the start of the active recharge pulse. The inverted pulse 550 terminates just after the stimulation pulse 506 since there is no need to also blank the peak of an active recharge pulse which is not occurring. Thus, the EVCP or other signal of interest may be sensed. The blanking control signal inverted pulse 550 thereby causes current flow to be blocked during the entire stimulation pulse 506 to produce the signal 554 once filtered. The signal 554 eliminates the artifacts from the stimulation pulse 506 as indicated by the region 552 while preserving the EVCP or other signal of interest. Therefore, the sensed physiological signals including the EVCP, EMG, etc. are present and recorded in the region 516 immediately after the stimulation pulse 506.

Figure 5C:
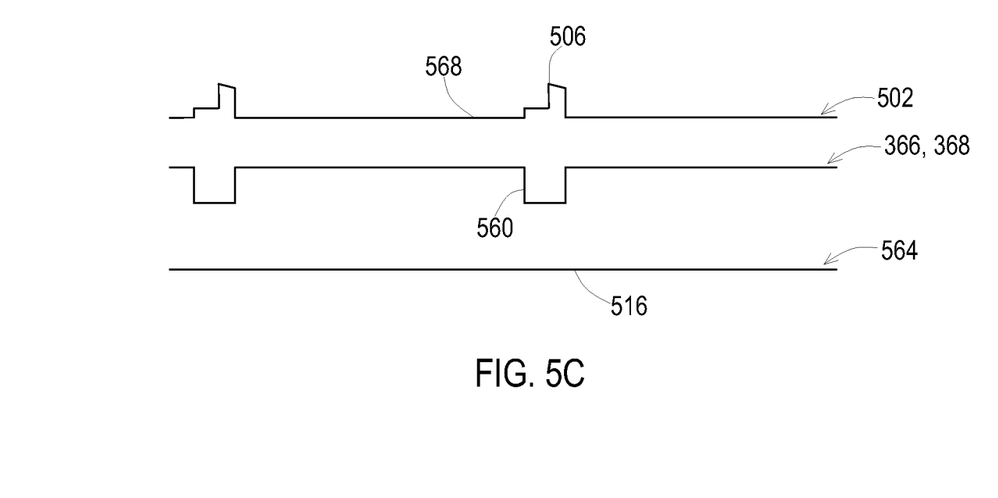
FIG. 5C shows a third example of the stimulation waveform, blanking signal, and the resulting artifact on the sensed signal.

FIG. 5C shows a set of signals and their related timing including the stimulation therapy waveform 502, the blanking control signal 366, 368, and the signal 564 that is provided to the amplifiers 312. As can be seen, the stimulation therapy waveform 502 includes a stimulation pulse 506 followed by an active recharge pulse 568 of opposite polarity with a lower amplitude and longer duration. The active recharge pulse 568 may be provided with a steady amplitude rather than a decaying amplitude like the passive recharge pulse, and the active recharge pulse 568 may also have a smaller amplitude than the peak of the passive recharge pulse. This allows the signal amplifiers to adequately capture the sensed signal while the active recharge pulse 568 is ongoing, particularly where the recharge pulse 568 has a longer duration than the signal of interest being sensed. If desired, the blanking can occur at the edges of the passive recharge pulse while sensing occurs during the relatively lengthy middle portion of the active recharge pulse 568.

The blanking control signal 366, 368 is held at an amplitude that biases the blanking control switches to the conducting state to allow current flow. However, the blanking control signal 366, 368 includes an inverted pulse 560 that unbiases the blanking control switches from the conducting state to the non-conducting state to prohibit current flow. In this example of FIG. 5C, the blanking control signal 366, 368 is synchronized in time to the stimulation waveform 502 such that the blanking control signal inverted pulse 560 begins just before the stimulation pulse 506 and terminates just after stimulation pulse 506 without the need to also blank the peak of a passive recharge pulse which is not occurring. Thus, the EVCP may be sensed here as well. The blanking control signal inverted pulse 560 thereby causes current flow to be blocked during the entire stimulation pulse 506 to produce the signal 564 once filtered. The signal 564 eliminates the artifacts from the stimulation pulse 506 as indicated by the region 562 while preserving the EVCP. Therefore, the sensed physiological signals including the EVCP are present and recorded in the region 516 immediately after the stimulation pulse 506.

Figure 6:
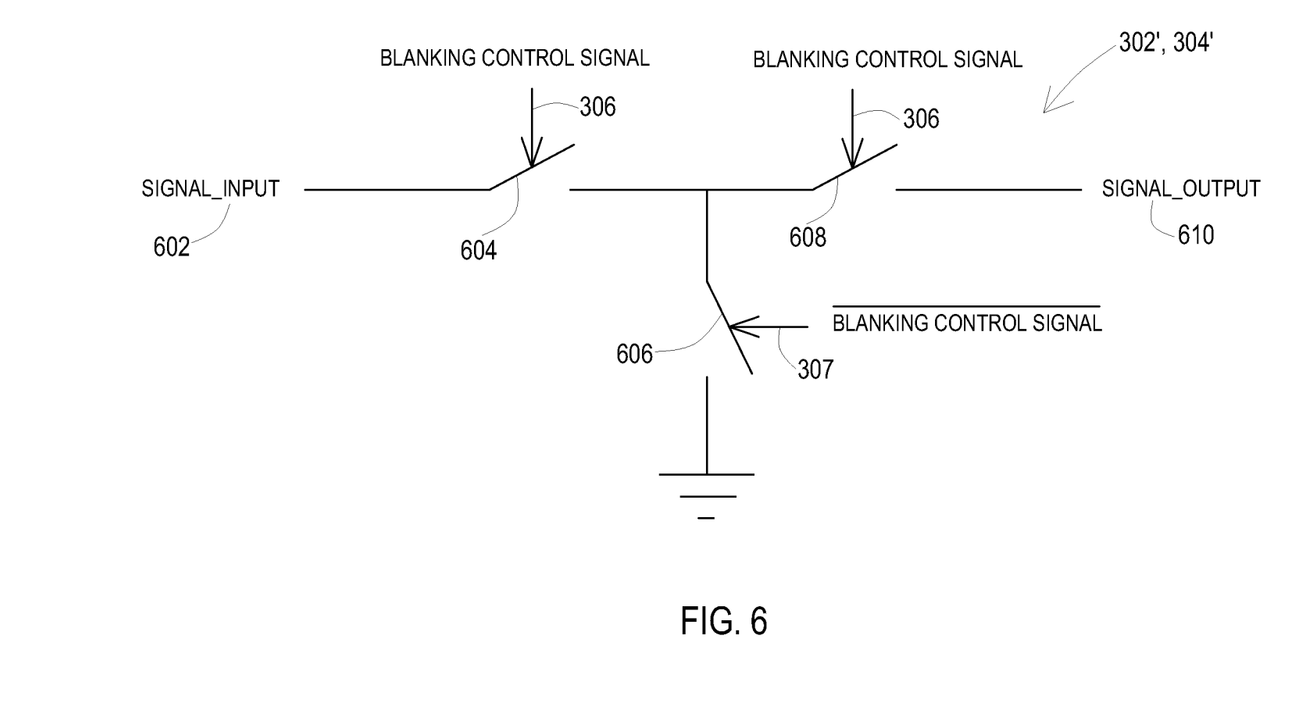
FIG. 6 shows an alternative design of the blanking switch of FIG. 3 that utilizes three switches.

FIG. 6 shows an alternate configuration of a blanking control switch 302', 304' for a given signal path in order to provide greater isolation between signal paths where multiple signal paths via multiple electrodes are present. Three individual switches ultimately provide the functionality of a single switch in the signal path. That is, a respective instance of the circuit of FIG. 6 may be substituted for each of switches 302 and 304 of FIG. 3. The signal 602 from the electrode 118 or 120 encounters a first series blanking control switch 604, a parallel-to-ground blanking control switch 606, and another series blanking control switch 608. The series switches 604, 608 are controlled by the blanking control signal 306 so as to conduct current except during the time including the stimulation pulse and the peak of the recharge pulse. The parallel switch 606 is controlled by an inverted blanking control signal 307 such that the switch 606 only conducts current during the time including the stimulation pulse and the peak of the recharge pulse to output a signal 610 to the filters 310. Thus, the node of the parallel switch 606 is grounded during the stimulation pulse and the peak of the recharge rather than floating.

Figure 7:
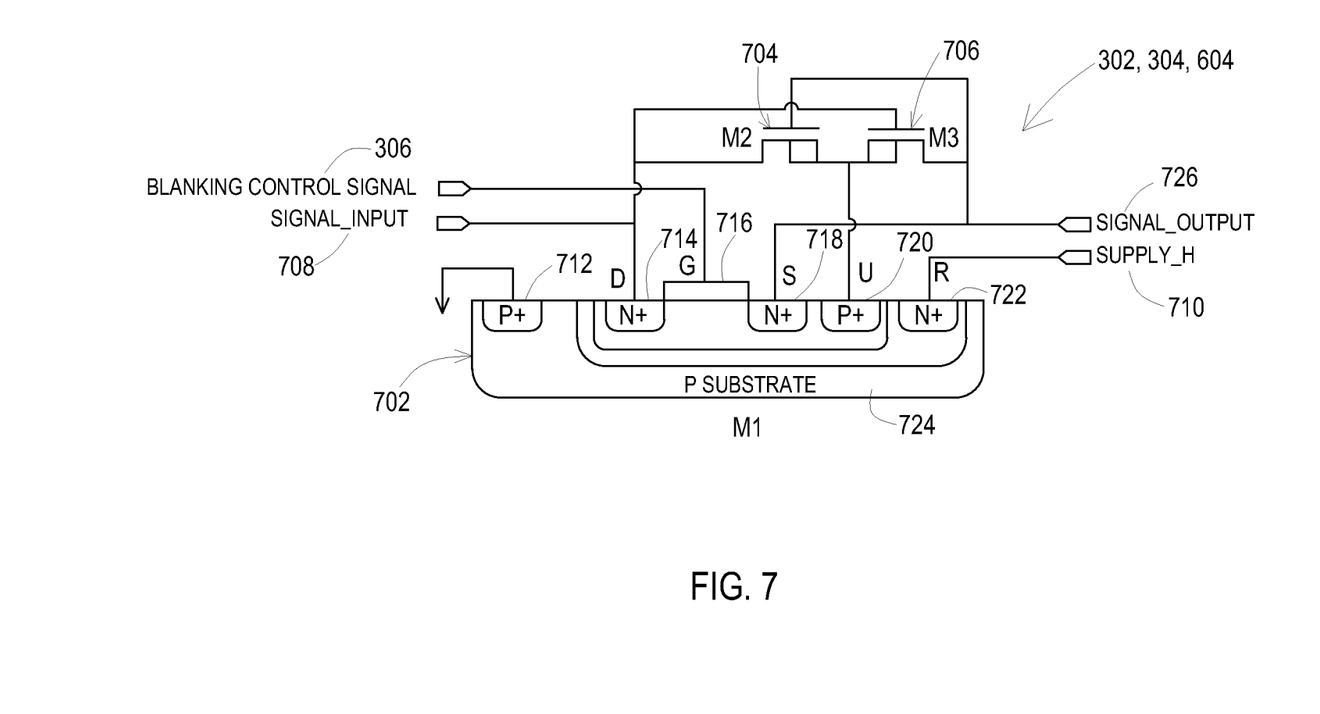
FIG. 7 shows an example of a design of an individual blanking switch as shown in FIGS. 3 and 6 or a limiting circuit as shown in FIG. 8.

FIG. 7 shows an example of a blanking switch configuration that may be used to implement any of switches 302, 304, 604, 606, and 608 discussed above in relation to FIGS. 3 and 6. This configuration may be particularly useful for the implementation of switches 302, 304, and 604, since these switches may receive relatively large amplitude signals. According to this example, the blanking switch is formed by the interconnection of three individual transistors 702, 704, 706 rather than a single one.

This configuration provides added safety to the blanking switches, particularly for switches 302, 304, 604 where the stimulation signal that is received by the sensing electrodes 118, 120 may be very large, such as in the case of defibrillation signals of cardiac devices. The M1 transistor 702 having a substrate 724 receives the sensed signal from the electrode 118 or 120 at a node 714 such as a FET drain, receives the blanking control signal from the controller 202 at a node 716 such as a FET gate, and outputs the sensed signal 726 when conducting from a node 718 such as a FET source. The n-well 722 receives a supply voltage 710 while the p-well 712 is to ground. The voltage across the p-well 720 of the M1 transistor 702 is set through the M2 transistor 704 and the M3 transistor 706, to be the lower voltage of the input and output of the M1 transistor 702, ensuring no forward biased well of the M1 transistor 702. This ensures the reliability of the blanking control switch 302, 304, 604 no matter the input voltage of the M1 transistor 702.

Figure 8:
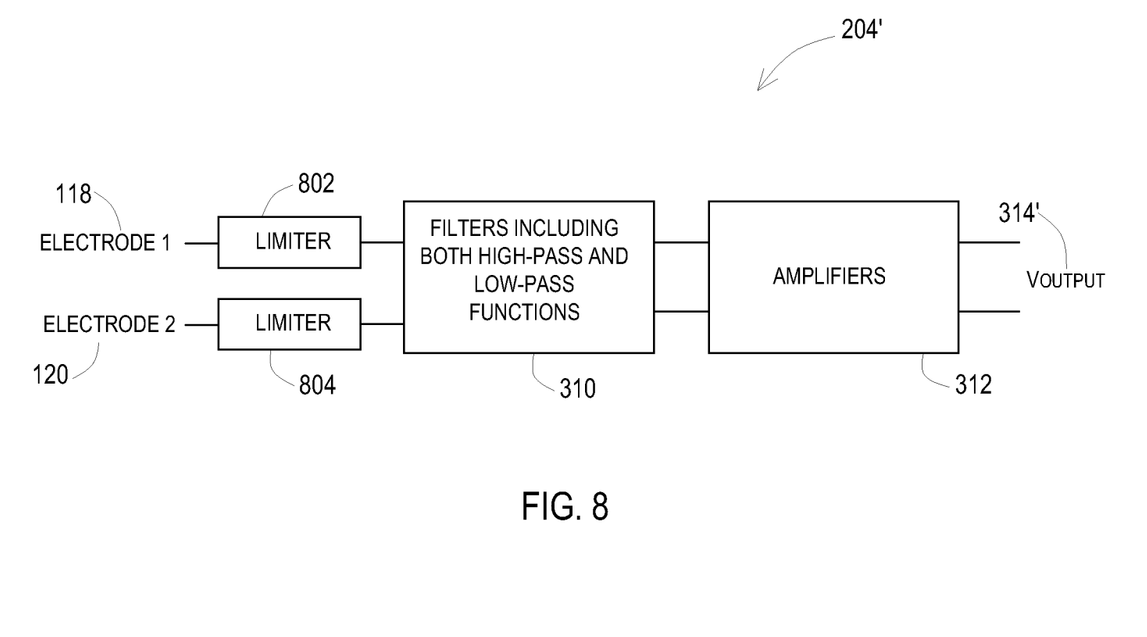
FIG. 8 shows an example of limiting circuitry of a medical device that limits the amplitude of the sensed signal during the stimulation signal.

As an alternative to blanking the stimulation signal, the sensing circuit 204 may instead employ signal limiting of the stimulation signal such that the amplitude of the sensed stimulation signal value, such as voltage, is small enough to not adversely affect the performance of the filters 310 and amplifiers 312. FIG. 8 shows an example of the sensing circuit 204' that limits the stimulation signal amplitude and the peak signal value, such as voltage, of the recharge signal. Each sensing electrode 118, 120 is electrically coupled to a signal limiter 802, 804 that is controlled by the controller 202. The limiters 802, 804 may be implemented in silicon such as individual transistors or in more complex arrangements as discussed below. The controller 202 may provide a DC value that sets a limit threshold of the limiters 802, 804 so that the signal level being passed to the filters does not exceed the limit threshold.

The limiters 802, 804 are followed in the signal path by the filters 310 that include both high pass and low pass filters that remove extraneous frequencies from the sensed signal. As discussed above, examples of the filters 310 are shown in FIGS. 4A and 4B. The filtered signals are provided as input to conventional amplifiers 312 that scale the amplitude as desired to produce the sensed signal output 314'. In this embodiment of the sensing circuit 204', the filters 310 include a high pass filter and a low pass filter.

Figure 9:
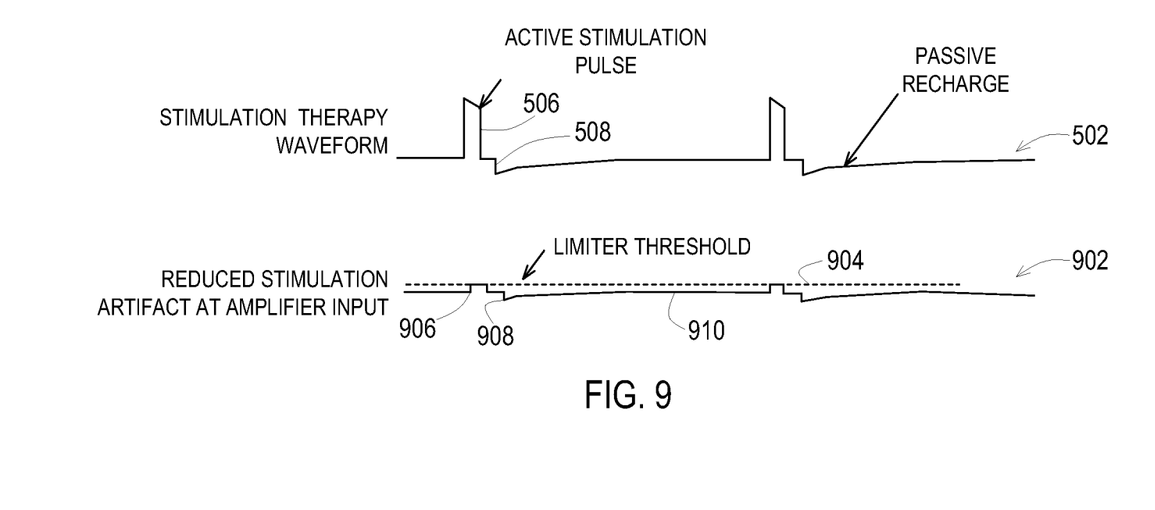
FIG. 9 shows an example of the stimulation waveform, the limiting threshold, and the resulting artifact on the sensed signal.

FIG. 9 show a set of signals including the stimulation therapy waveform 502, the limiting threshold value 904, and the signal 902 that is provided to the amplifiers 312 for this limiter embodiment. The stimulation therapy waveform 502 includes the stimulation pulse 506 followed by the passive recharge pulse 508 of opposite polarity with a lower amplitude and longer settling time. Again, the recharge pulse could instead be active and in that case could more closely match the amplitude and settling time of the stimulation pulse.

The limiting threshold value 904 is continuously held at a constant amplitude that limits the voltage being output to the filters 310 to produce the signal 902 once filtered. The signal 902 largely eliminates the artifacts from the stimulation pulse 506 as indicated by the small pulse 908 that results from the occurrence of the larger amplitude stimulation pulse 506. The small pulse 908 is not large enough to saturate the filters 310 and amplifiers 312. Signal 902 also includes the small artifact 908 from the tail of the recharge pulse 508 which is also not large enough to saturate the filters 310 and amplifiers 312. Thus, the sensed physiological signals are present and recorded in the region 910 upon the recharge pulse 508 having adequately settled soon after the peak.

The limiter may be implemented in a similar manner as the blanking switch 302, 304 including any of the aspects shown in FIGS. 3, 6, and 7, including the multiple switch configurations but with a change to the blanking control signal. Through blanking control signals 306, 308 in FIG. 3 or through blanking control signal 306 in FIG. 6, these blanking control signals may provide a continuous limiting voltage (VLimiter) can be applied as the limiting threshold in place of the binary blanking control signal. Therefore any input signal greater than (VLimiter−Vt) will be limited to (VLimiter−Vt) on the output, where Vt is the MOSFET threshold voltage for conduction.

While embodiments have been particularly shown and described, it will be understood by those skilled in the art that various other changes in the form and details may be made therein without departing from the spirit and scope of the invention.

What is claimed is:

1. A method of sensing physiological signals while stimulation therapy is being provided by using a device that comprises:
   a sensing electrode;
   a blanking switch;
   a first electrically conductive pathway connected between the sensing electrode and the blanking switch;
   a sensing amplifier;
   a second electrically conductive pathway connected between the sensing amplifier and the blanking switch;
   a controller, the method comprising:
   while a stimulation signal having a stimulation phase and a recharge phase is being output from a first electrode at a stimulation site, sensing a physiological signal at a second electrode in proximity to the stimulation site to produce a sensed signal; and
   during at least a portion of the recharge phase and a next stimulation phase of the stimulation signal that follows the recharge phase, the controller maintains the blanking switch in a non-conducting state to blank the sensed signal and during at least the portion of the recharge phase and the next stimulation phase, the controller maintains the blanking switch in a conducting state thereby not blanking the sensed signal for a period of time after the next subsequent stimulation phase that follows the recharge phase and prior to a next recharge phase that follows the next stimulation phase, the next recharge phase occurring prior to any stimulation phase that occurs after the next stimulation phase, the period of time that the controller maintains the blanking switch in the conducting state being longer than an amount of time between an end of the recharge phase and a beginning of the next stimulation phase that follows the recharge phase.

2. The method of claim 1, wherein the device includes a filter electrically connected between the sensing electrode and the sensing amplifier.

3. The method of claim 2, wherein the controller further blanks the sensed signal by opening a second switch in series between the blanking switch and the filter and closing a third switch in parallel with the blanking switch and the second switch.

4. The method of claim 2, wherein the filter comprises a low pass filter and a high pass filter.

5. A device for sensing a physiological signal while stimulation therapy is being provided, comprising:
- a sensing electrode;
- a blanking switch;
- a first electrically conductive pathway connected between the sensing electrode and the blanking switch;
- a sensing amplifier;
- a second electrically conductive pathway connected between the sensing amplifier and the blanking switch; and
- a controller that maintains the blanking switch in a non-conducting state during at least a portion of the recharge phase and a next stimulation phase of a stimulation signal that follows the recharge phase and that maintains the blanking switch in a conducting state for a period of time after the next stimulation phase that follows the recharge phase and prior to a next recharge phase that follows the next stimulation phase, the next recharge phase occurring prior to any stimulation phase that occurs after the next stimulation phase, the period of time that the controller maintains the blanking switch in the conducting state being longer than an amount of time between an end of the recharge phase and a beginning of the next stimulation phase that follows the recharge phase.

6. The device of claim 5, further comprising a filter, wherein the filter comprises a low pass filter and a high pass filter positioned electrically between the blanking switch and the sensing amplifier.

7. The device of claim 5, further comprising a stimulation engine, and wherein the controller triggers the stimulation engine to produce a stimulation pulse of the next stimulation phase.

8. The device of claim 7, wherein the controller triggers the stimulation engine to produce the recharge phase of the stimulation signal in response to detecting a time for the presence of the recharge phase.

9. The device of claim 5, wherein the blanking switch comprises a plurality of individual switches.

10. A device for sensing a physiological signal while stimulation therapy is being provided, comprising:
- a sensing electrode;
- a blanking switch;
- a first electrically conductive pathway connected between the sensing electrode and the blanking switch;
- a sensing amplifier;
- a second electrically conductive pathway connected between the sensing amplifier and the blanking switch; and
- a controller that maintains the blanking switch in a non-conducting state during at least a portion of a recharge phase and a next stimulation phase of a stimulation signal that follows the recharge phase and that maintains the blanking switch in a conducting state for a period of time after the next stimulation phase that follows the recharge phase and prior to a next recharge phase that follows the next stimulation phase, the next recharge phase occurring prior to any stimulation phase that occurs after the next stimulation phase, the period of time that the controller maintains the blanking switch in the conducting state being longer than an amount of time between an end of the recharge phase and a beginning of the next stimulation phase that follows the recharge phase, wherein the recharge phase comprises an active recharge pulse.

11. The device of claim 10, wherein the controller starts an instance of blanking of at least a portion of the active recharge pulse and continues the instance of blanking until a stimulation pulse occurring after the active recharge pulse ends.

12. The device of claim 11, wherein the active recharge pulse begins after an evoked compound potential (EVCP) portion of the sensed signal, and wherein sensing comprises sensing the EVCP portion.

* * * * *